US00RE43526E

(19) United States
(12) Reissued Patent
Morrison et al.

(10) Patent Number: US RE43,526 E
(45) Date of Reissued Patent: Jul. 17, 2012

(54) ROD INTRODUCTION APPARATUS

(75) Inventors: Matthew M. Morrison, Cordova, TN (US); Eric A. Loveless, Jacksonville, FL (US); David L. Brumfield, Southaven, MS (US); B. Thomas Barker, Memphis, TN (US); Catalina J. Carroll, Memphis, TN (US); David Miller, Eads, TN (US); Dominique Petit, Sur Mer (FR)

(73) Assignee: Warsaw Orthopedic, Inc., Warsaw, IN (US)

(21) Appl. No.: 12/052,465

(22) Filed: Mar. 20, 2008

Related U.S. Patent Documents

Reissue of:
(64) Patent No.: 5,910,141
Issued: Jun. 8, 1999
Appl. No.: 08/798,092
Filed: Feb. 12, 1997

(51) Int. Cl.
*A61B 17/56* (2006.01)

(52) U.S. Cl. ..... 606/86 A

(58) Field of Classification Search ..... 606/246, 606/264, 265, 278, 279, 86 R, 99, 100, 101, 606/86 A, 300, 305
See application file for complete search history.

(56) References Cited

U.S. PATENT DOCUMENTS

| | | | | |
|---|---|---|---|---|
| 3,604,487 A | | 9/1971 | Gilbert | |
| 3,844,291 A | | 10/1974 | Moen | |
| 4,411,259 A | | 10/1983 | Drummond | |
| 5,020,519 A | * | 6/1991 | Hayes et al. | 606/237 |
| 5,113,685 A | * | 5/1992 | Asher et al. | 72/458 |
| 5,209,755 A | | 5/1993 | Abrahan et al. | |
| 5,308,357 A | | 5/1994 | Lichtman | |
| 5,314,431 A | * | 5/1994 | Graziano | 606/101 |
| 5,330,472 A | | 7/1994 | Metz-Stavenhagen | |
| 5,364,397 A | | 11/1994 | Hayes et al. | |
| 5,389,099 A | * | 2/1995 | Hartmeister et al. | 606/86 A |
| 5,392,978 A | | 2/1995 | Velez et al. | |
| 5,423,855 A | * | 6/1995 | Marienne | 606/208 |
| 5,449,361 A | | 9/1995 | Preissman | |
| 5,458,608 A | | 10/1995 | Wortrich | |
| 5,466,243 A | | 11/1995 | Schmieding et al. | |
| 5,588,580 A | | 12/1996 | Paul et al. | |
| 5,616,143 A | | 4/1997 | Schlapfer et al. | |
| 5,720,751 A | * | 2/1998 | Jackson | 606/86 R |

(Continued)

FOREIGN PATENT DOCUMENTS

DE 4238339 5/1994

(Continued)

OTHER PUBLICATIONS

Compact CD Low Back Surgeon's Documentation, Sofamor Spine Division, pp. 60-61, 78-79. Date unknown.*

(Continued)

*Primary Examiner* — Eduardo C Robert
*Assistant Examiner* — David Comstock

(57) ABSTRACT

An introduction apparatus for approximating a longitudinal member and an implant to permit fixation therebetween. The introduction apparatus having a gripping nose for securely engaging an implant, a lateral approximation mechanism for laterally aligning an implant and an offset longitudinal member, and a reduction mechanism for reducing the vertical distance between the implant and the longitudinal member. The introduction apparatus is provide with a gripping nose actuated by axial movement of a clamping shaft in an outer sleeve. The clamping shaft further includes an axial cannula for passage of a fastener to the implant.

39 Claims, 10 Drawing Sheets

U.S. PATENT DOCUMENTS

| | | | |
|---|---|---|---|
| 5,782,830 | A | 7/1998 | Farris |
| 5,782,831 | A | 7/1998 | Sherman et al. |
| 5,810,878 | A | 9/1998 | Burel et al. |
| 5,855,311 | A | 1/1999 | Hamblin et al. |
| 5,899,901 | A | 5/1999 | Middleton |
| 5,944,720 | A | 8/1999 | Lipton |
| 6,036,692 | A | 3/2000 | Burel et al. |
| 6,042,582 | A | 3/2000 | Ray |
| 6,063,088 | A | 5/2000 | Winslow |
| 6,261,296 | B1 | 7/2001 | Aebi et al. |
| 6,440,133 | B1 | 8/2002 | Beale et al. |
| 6,790,209 | B2 | 9/2004 | Beale et al. |
| 6,830,570 | B1 | 12/2004 | Frey et al. |
| 7,156,849 | B2 | 1/2007 | Dunbar et al. |
| 7,470,279 | B2 | 12/2008 | Jackson |
| 7,611,517 | B2 | 11/2009 | Lim |
| 7,625,376 | B2 | 12/2009 | Brumfield et al. |
| 2004/0267275 | A1 | 12/2004 | Cournoyer et al. |
| 2005/0192570 | A1 | 9/2005 | Jackson |
| 2005/0192579 | A1 | 9/2005 | Jackson |
| 2005/0228400 | A1 | 10/2005 | Chao et al. |
| 2006/0036244 | A1 | 2/2006 | Spitler et al. |
| 2006/0074418 | A1 | 4/2006 | Jackson |
| 2006/0111712 | A1 | 5/2006 | Jackson |
| 2006/0173454 | A1 | 8/2006 | Spitler et al. |
| 2007/0270867 | A1 | 11/2007 | Miller et al. |
| 2007/0270868 | A1 | 11/2007 | Dewey |
| 2007/0276379 | A1 | 11/2007 | Miller et al. |
| 2008/0077139 | A1 | 3/2008 | Landry et al. |
| 2008/0091213 | A1 | 4/2008 | Jackson |
| 2008/0234678 | A1 | 9/2008 | Gutierrez et al. |
| 2008/0234765 | A1 | 9/2008 | Frasier et al. |

FOREIGN PATENT DOCUMENTS

| | | | | |
|---|---|---|---|---|
| RU | 995769 | * | 2/1983 | ..... 606/101 |

OTHER PUBLICATIONS

The RSRH Minicordscrew, pp. 50-51, ch. 2. Date unknown.*
Cortel-Dubousset Instrumentation (1 page). Date unknown.*
Universal Spinal System Rod Introduction Pliers by Synthes Spine (13 pages). Date unknown.*
Sofamor, "Introducteur—Contreur De Tige" (schematic drawings), Jan. 1, 1994.
Laufer and Bowe, CD Horizon Spinal System, Surgical Technique, 1996, Sofamor Danek.
TSRH-3D Vertebral Body Reduction Instrumentation, 2001, Medtronic Sofamor Danek.
Shufflebarger et al., Taking Spinal Instrumentation to a New Dimension, 1995.
Moss® Miami 3-Dimensional Instrumentation Product Catalogue, 1995, Depuy Motech, Inc.
Pediatric Isola® Spinal System, Ordering Information for Implants and Instruments, 1998, AcroMed Corporation.
Orthopedic Sourcebook, Instruments for Surgeons, Section K, 1999, Medic.
Z Spinal Instrumentation, Section D, 1987, Zimmer, Inc.
Sofamor Rod Reducer (1994).
Universal Spinal System Rod Introduction Pliers by Synthes Spine (13 Pages).
Pages 50-51, Chapeter 2,The TSRH Minicorkscrew.

* cited by examiner

ROD INTRODUCTION APPARATUS

Matter enclosed in heavy brackets [ ] appears in the original patent but forms no part of this reissue specification; matter printed in italics indicates the additions made by reissue.

*This application is a reissue of U.S. Pat. No. 5,910,141, issued on Jun. 8, 1999, which is hereby incorporated by reference, as if fully set forth herein. U.S. Pat. No. 5,910,141 matured from U.S. application Ser. No. 08/798,092, filed Feb. 12, 1997.*

BACKGROUND OF THE INVENTION

1. Description of the Prior Art

The present invention relates generally to instruments used to manipulate orthopedic implants. More particularly, the present invention relates to the manipulation of hone anchoring elements positioned in the spine and longitudinal members interconnecting those elements. While the present invention is particularly useful in spinal surgery, it may find use in other areas of medicine as well.

In many applications, particularly those relating to spinal correction techniques, it is desirable to place a series of implants in a patient's spine prior to inserting a longitudinal member (a rod or a plate) along the spine to interconnect the previously placed implants. On occasion, implants may be vertically spaced from the rod or plate and require a mechanical mechanism to bring the rod or plate into contact with the implant. In the instance of a plate, often the implant is a double threaded bolt with a series of bone screw threads anchoring into the bone and a machine threaded post extending through an opening in the plate. A machine threaded nut slightly larger than the opening in the plate may then be threaded onto the threaded post and tightened to bring the implant closer to the plate. For rod systems, a similar arrangement can be utilized whereby the threaded post of the implant extends through a connector attached to the rod. In these systems a nut is used to draw the implant closer to the connector by progressively threading the nut onto the post of the bone bolt.

Alternatively, it is known to provide a rod introducer mechanism that forces the rod and an implant towards each other. In some cases, the threaded post of a bolt type bone anchor is not long enough to extend through a connector attached to the rod. In this situation a mechanism is used to grasp the bolt and pull it towards the connector until the threaded post extends through an opening in the connector. A threaded nut may then be used to complete the connection to the connector.

In other cases the implant, either a bone screw or spinal hook, includes an open channel to receive the rod. A plug or set screw can be used to close the channel and lock the rod to the implant. In certain surgical techniques a rod is anchored at both ends by at least one implant, resulting in the rod being suspended above a second implant. A mechanism is then required to urge the second implant and rod together to permit connection of the implant to the rod and more particularly to seat the rod within the open channel of the implant. One such instrument marketed by Sofamor Danek Group as part of the Compact CD™ system, is an introducer lever C-6903 which resembles a fork with a pair of offset tines. The tines of this device extend over the vertically spaced rod and under either side of an enlarged portion of the implant. Once in place, the fork handle is moved toward the rod thereby forcing the rod and implant together. One problem with this arrangement is that the fork tines must pass between the implant and the bone, which in many cases may be difficult and may result in damage to the bone. Moreover, the connection between the fork tines and the implant is not a secure engagement and may result in the rod introducer slipping during the procedure of forcing the rod into the implant.

Other types of rod introduction devices have overcome the problems associated with the simple fork device by first achieving a secure attachment to the implant with articulated forceps or the like. Various instruments for gripping and handling implants are commonly known. One such instrument has a pair of articulating branches defining a gripping nose opposite a pair of handles. While many varieties of these forceps exist to accomplish various functions during surgery, some are adapted specifically to securely hold an implant, and in particular, a spinal osteosynthesis implant. The gripping nose of one such configuration utilizes a pair of inwardly facing cylindrical projections disposed at the distal end of the gripping nose. The cylindrical projections are adapted to engage corresponding recesses on an implant, thereby providing a secure grip. Because of the small size of many spinal implants and the accompanying difficulty gaining a secure grip with only manual pressure, such forceps are often utilized in the manipulation and placement of the implants.

In addition to providing a nose for gripping implants, many forceps also provide a locking mechanism to hold the forceps in the gripping position once the implant is gripped. A common example is the provision of one half of a ratchet rack on one articulating branch aligned to engage a second half of the ratchet rack on the other articulating branch. Upon movement of the branches towards one another, the separate halves of the ratchet rack come into engagement thereby preventing separation of the articulating branches. As is common with such arrangements, the articulating branches have sufficient flexibility that they may be flexed with respect to one another, thereby disengaging the ratchet racks.

An alternative forcep locking mechanism is disclosed in U.S. Pat. No. 5,423,855 owned by the Sofamor SNC subsidiary of Sofamor Danek Group. This patent shows forceps having an implant gripping nose as previously discussed. In this configuration, the articulating branches are held in the closed position by a spring biased cap disposed on the end of the branches opposite the gripping nose.

In prior systems, once a secure engagement has been accomplished between the forceps and the implant, a separate apparatus is attached between the forceps and the rod. In one such mechanism marketed by Sofamor Danek Group as the TSRH™ mini-corkscrew, a threaded rod is threadedly coupled at one end to the forceps and engages the rod at the opposite end. Rotation of the threaded rod urges the rod and implant towards each other. In another mechanism marketed by Sofamor Danek Group as an articulated rod pusher C-6211 for use with the Compact CD™ system, forceps grip the implant and a pivoting two piece rod pusher lever is used to urge the rod and implant towards one another. In this device, a lower end of the first member of the rod pusher engages the rod and the upper end of the first member is pivotally attached to the second member of the rod pusher lever. The lower end of a second member engages the forceps while the upper end of the second member is rotated to force the rod and implant towards each other.

U.S. Patent 5,020,519 to Hayes et al. discloses a single mechanism which both grips the rod and has a threaded mechanism to accomplish vertical reduction of the rod into the implant. As this reference discloses, the mechanism must first be attached to the implant and then the rod threaded through the opening between the clamping jaws. This unnecessarily creates a complication for the surgeon, i.e. maintaining both the reduction mechanism and the hook in the desired position while attempting to thread the rod through various implants and the opening in the reduction apparatus. Moreover, once the rod has been reduced into the implant opening, the reduction apparatus interferes with visualizing the implant and rod connection, and with placement of a fastener to hold the rod in the implant.

In addition to the surgical condition where the rod is suspended above the implant, the rod may be laterally offset with respect to the implant. Moreover, in some applications the implant may have an implant opening for receiving the rod which opens to the side, thereby requiring the rod to be laterally introduced into the implant. In these instances, it is often desirable to have mechanical assistance in bringing the rod and implant together to permit securing the rod within the implant. One such device marketed by Synthes Spine as the Universal Spinal System Rod Introduction Pliers is utilized to urge a laterally offset rod into a side opening implant. The Rod Introduction Pliers are used in conjunction with a Hook or Screw Holder device threadedly engaging the implant. One branch of the pliers consists of a barrel while the opposing branch defines a rod engaging surface. In operation, this barrel is placed over the Hook or Screw Hold device and the opposing branch of the pliers engages the offset rod and upon actuation of the plier handles the rod is urged into the implant opening. While this system provides a means to reduce the lateral displacement of the rod, it does not permit the user to additionally reduce any vertical displacement between the rod and the implant. Rather, the barrel of the rod introduction pliers apparently slides freely up and down the hook holder.

In addition to having a need, in some surgical situations, to both laterally approximate the rod to the implant and to vertically reduce the rod into the implant, there is a need to deliver a fastening member to the implant while the rod is securely held in place by the rod reduction apparatus. In some systems, the components required to accomplish reduction are offset with respect to the implant, thereby providing access to the implant to facilitate placement of the fastener once the rod is inserted into the implant. Use of offset instruments to apply force to the rod and implant may impart rotational forces to the implant tending to displace the implant from the desired location. Moreover, in most applications the fastening elements must be relatively small to prevent unnecessary protrusion from the implant. While this is desirable after placement, the small size of the fastener makes handling these items difficult. The difficulty of handling the small fasteners is increased when it is required to place them in the implant that is partially obscured by the rod introduction device. One approach to solving this problem is taken by the Universal Spine System pliers discussed above. In operation, a fastening collar is preloaded over the barrel prior to placement over the hook holder. Once the rod has been inserted into the implant the collar may be advanced over the barrel and engaged with the implant.

One disadvantage to the systems discussed above, is that none of the systems provide both a mechanism for reducing vertical rod offset and lateral rod offset from the bone anchor in a single device. Moreover, many of the systems utilize articulating clamping tips actuated by articulating handles to hold the implants and require a separate apparatus attached to the hook or screw holder to perform manipulation of the rod. It will be appreciated that the various handles extending out of the patient interfere both with vision and work space in an already limited surgical field. Therefore, it is desirable to provide a compact implant holder adapted to perform both vertical and lateral reduction of a rod.

The present invention overcomes the problems associated with the prior art by providing a gripping mechanism and a rod introduction lever for both lateral and vertical approximation in a single convenient instrument.

SUMMARY OF THE INVENTION

One form of the present invention contemplates a multiple action insertion apparatus for engaging a longitudinal member and an implant, comprising an implant holder including a first clamping branch and a second clamping branch cooperable with the first clamping branch to hold to the implant, a reduction mechanism interconnected with the implant holder, the reduction mechanism having a distal end for engaging the longitudinal member, wherein the reduction mechanism urges the longitudinal member into vertical alignment with the implant, and a lateral approximator mechanism interconnected with the implant holder, the lateral approximator mechanism having a distal end disposed adjacent the first and second clamping branches, said distal end adapted to engage the longitudinal member, wherein said lateral approximator mechanism urges the longitudinal member into lateral alignment with the implant.

Still a further form of the present invention contemplates a multiple action insertion apparatus for engaging a longitudinal member and an implant, comprising a device for attaching to an implant having an opening for receiving a rod, a device for lateral approximation of a longitudinal member laterally offset from the implant rod opening, the device for lateral approximation interconnected with the device for attaching, and a device for vertical reduction of a longitudinal member vertically offset from the implant, the device for vertical reduction interconnected with the device for attaching, wherein the device for lateral approximation laterally aligns the longitudinal member over the implant and the device for vertical reduction vertically aligns the longitudinal member with the implant.

Another form of the invention contemplates an implant holder for holding an implant adapted to receive a fastener, comprising a device for gripping the implant, the device for gripping including a gripping end and a handle defining a longitudinal cannula having a distal end adjacent the gripping end, the cannula adapted to receive a fastener cooperable with the implant.

In another aspect, the present invention contemplates an implant holder for gripping an implant, comprising a shaft having a gripping end with a portion, the gripping end defining a first clamping branch and a cooperable second clamping branch, the first and second clamping branches tending to assume an insertion position defining a first distance between the first and second clamping branches, and the first and second clamping branches compressible into a clamping position defining a second distance between the first and second clamping branches, the first distance greater than the second distance, and a sleeve defining an interior channel, the shaft slidably received within the interior channel, the shaft moveable between a first position with the portion extending from the sleeve and a second position with the portion drawn into the sleeve, wherein movement of the shaft within the tubular sleeve from the first position to the second position controls the first and second clamping branches from the insertion position to the clamping position.

Another form of the present invention contemplates an implant holder having a rod reduction mechanism for vertically aligning a longitudinal member and an implant, comprising a device for gripping the implant, a sleeve having an axis and a distal end adapted to engage the longitudinal member, the sleeve having an axial bore sized to receive the device for gripping, the device for gripping slidably received within the axial bore, and a device for axially displacing the sleeve with respect to the device for gripping, whereby the vertical offset longitudinal member is urged into alignment with the implant.

Additionally, the invention includes a method for for interconnecting a longitudinal member and an implant adapted to engage the longitudinal member, comprising the steps of providing an introduction apparatus having an attachment mechanism with a cannula and a vertical reduction mechanism, attaching the introduction apparatus to the implant, operating the vertical reduction mechanism to force the longitudinal member into alignment with the implant, inserting a fastener through the cannula, interconnecting the fastener and the implant, wherein the longitudinal member is securely attached to the implant, and removing the introduction apparatus.

The invention includes an additional method for interconnecting a longitudinal member and an implant adapted to engage the longitudinal member, comprising the steps of providing an introduction apparatus having an attachment mechanism, a lateral approximation lever, and a vertical reduction mechanism, attaching the introduction apparatus to the implant, engaging a laterally offset longitudinal member with one end of the lateral approximator lever, rotating the lever to urge the longitudinal member into lateral alignment with the implant, operating the vertical reduction mechanism to force the longitudinal member into vertical alignment with the implant, and interconnecting the longitudinal member and the implant.

One object of the present invention is to provide an implant holder having a cannula for passage of a fastener to the implant while it is being securely held.

Another object of the present invention is to provide a simple device for gripping the implant and reducing vertical offset between an implant and a longitudinal member.

A further object of the present invention is to provide an implant holder operable in a small lateral area to clamp an implant by axial movement of the holder mechanism.

Still a further object of the present invention is to provide a multiple action insertion apparatus that is capable of gripping an implant, approximating the implant and an laterally offset longitudinal member, and reducing the vertical distance between the implant and the longitudinal member.

Another object of the present invention is to provide a multiple action insertion apparatus that is capable of gripping an implant, approximating the implant and an laterally offset longitudinal member, and reducing the vertical distance between the implant and the longitudinal member wherein the apparatus includes a cannula for insertion of a fastening member.

Related objects and advantages of the present invention will be apparent from the following description.

DESCRIPTION OF THE PREFERRED EMBODIMENTS

Figure 1:
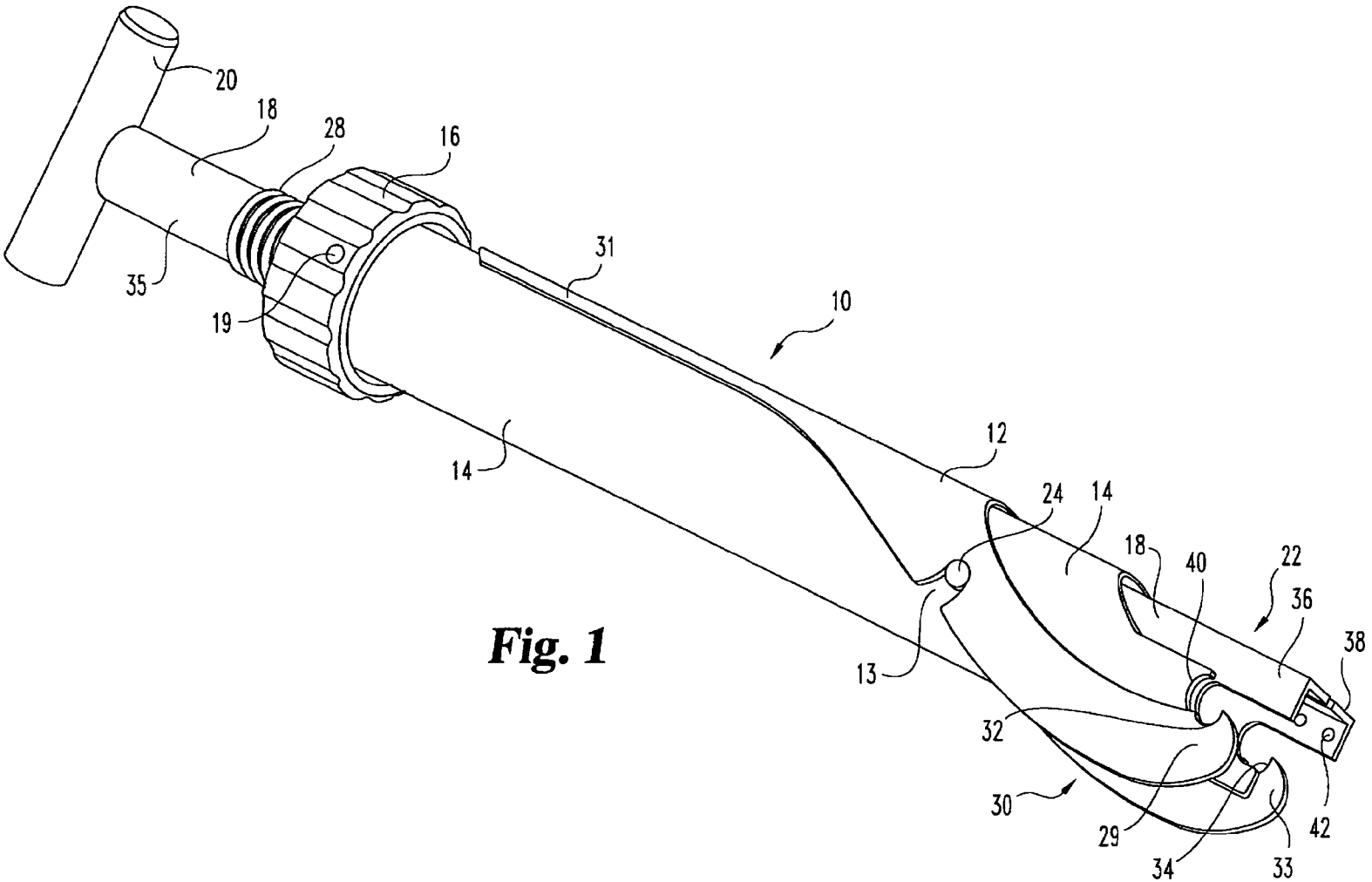
FIG. 1 is a perspective view of the rod introduction apparatus according to the present invention.

For the purposes of promoting an understanding of the principles of the invention, reference will now be made to the embodiments illustrated in the drawings and specific language will be used to describe the same. It will nevertheless be understood that no limitation of the scope of the invention is thereby intended, such alterations and further modifications in the illustrated device, and such further applications of the principles of the invention as illustrated therein being contemplated as would normally occur to one skilled in the art to which the invention relates.

Referring now to FIG. 1, a rod introduction apparatus 10 according to the present invention includes an outer sleeve 14, a clamp shaft 18 and a lateral approximator lever 12. As will be appreciated by the detailed description that follows, the rod introduction apparatus is a multiple action device having the capability of securely holding an implant (often a hook or a screw), aligning a laterally offset longitudinal member (typically a rod or a plate), reducing the vertical distance between the longitudinal member and the implant, and providing a passage for placement of a fastener into the implant while the implant and longitudinal member are held in alignment. It is understood that all of the features of the apparatus may be used in combination or only a select portion thereof may be utilized, the features utilized will depend on the needs of the surgery being performed.

Figure 6:
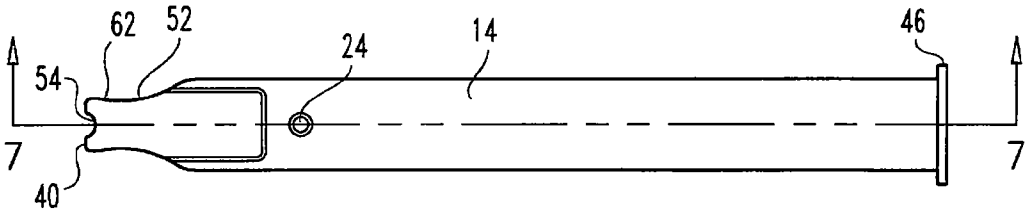
FIG. 6 is a side view of the rod introduction sleeve.

Referring now to FIGS. 5 through 8, outer sleeve 14 includes on its proximal end a shoulder 46 extending around the entire circumference of the outer sleeve. Pivot pins 24 and 25 project from opposite sides of the outer sleeve. The distal end of outer sleeve 14 is the rod engagement end 40, which defines a pair of diametrically opposed rod engagement arms 62 and 63. As shown in FIG. 6, these arms have a substantially reduced width 52 in comparison to diameter of outer sleeve 14, as they extend towards the rod engagement end 40. Disposed on the distal tip of rod engagement arm 62 is a concave recess 54 having a curvature substantially equivalent to the outside diameter of a rod. A similar concave recess 55 is disposed on the distal tip of rod engagement arm 63 and is in alignment with concave recess 54 to permit a rod to be engaged by both recesses simultaneously. It will be understood that rod engaging arms 62 and 63 have concave recesses 54 and 55 in order to hold a portion of the rod and inhibit lateral movement thereof.

Figure 7:
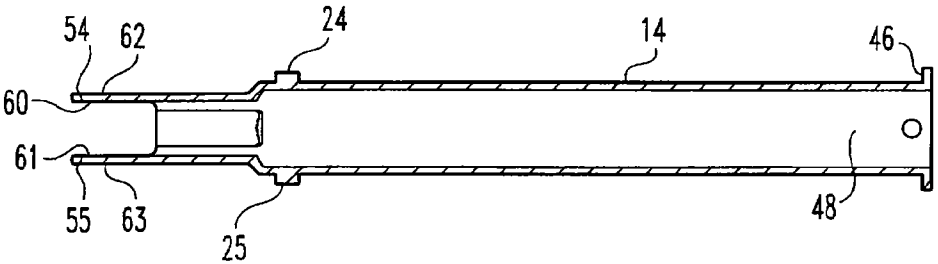
FIG. 7 is a cross-sectional view taken along section lines 7—7.
Figure 8:
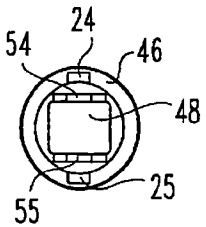
FIG. 8 is an end view of the rod introduction sleeve looking into the rod bearing surface.

FIG. 7 shows a cross-sectional view of outer sleeve 14. The outer sleeve is a hollow substantially cylindrical tube defining an interior channel 48 extending therethrough. Interior channel 48 is substantially narrowed adjacent the distal end by inner surfaces 60 and 61 of rod engagement arms 62 and 63, respectively. As shown in FIG. 8, an end view of outer sleeve 14 looking into the distal end, the inner sidewalls of outer sleeve 14 can form a substantially rectangular surface defining interior channel 48.

Figure 9:
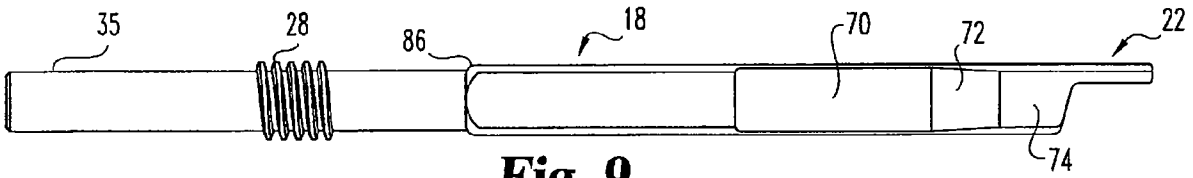
FIG. 9 is a side view of a rod introduction clamp shaft.
Figure 10:
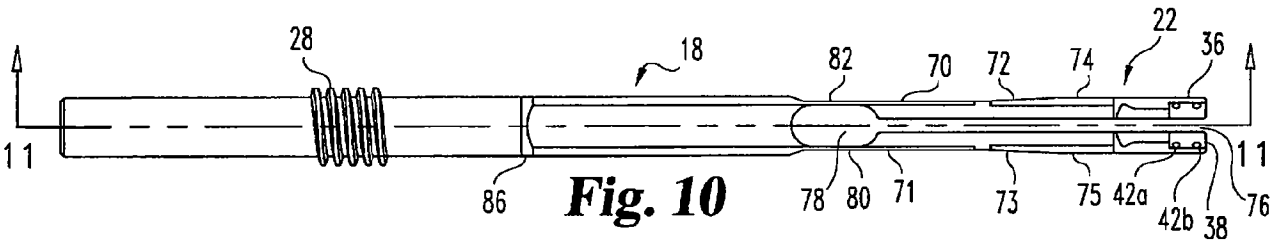
FIG. 10 is a bottom view of the rod introduction clamp shaft.

Referring now to FIGS. 9 through 11, clamp shaft 18 is sized to be slidingly received within the interior channel of outer sleeve 14. Clamp shaft 18 includes gripping nose 22 having a portion extendable beyond the distal end of outer sleeve 14. Gripping nose 22 includes a first clamping branch 36 and a second clamping branch separated by space 76. The distance between first clamping branch 36 and second clamping branch 76 changes as the clamping branches are moved from there insertion position, with ramped sidewall portion extending outside outer sleeve 14, to a clamping position with ramped sidewall portions 72 and 73 engaging bearing surfaces 60 and 61 respectively. In the preferred embodiment the clamping branches resiliently tend to assume there insertion form unless constrained by outer sleeve 14. Preferably, clamping branches 36 and 38 have an area of reduced wall thickness defining a void 78 adjacent their attachment points to the remainder of clamping shaft 18. This area of reduced wall thickness tends to experience the greatest amount of deflection when the clamping branches are in the clamping position. While the preferred embodiment relies on the resiliency of the clamping branches themselves to assume the insertion position, it is contemplated that a mechanical means cooperable with the clamping branches may be utilized to move the clamping branches between the insertion and clamping positions.

Figure 2:
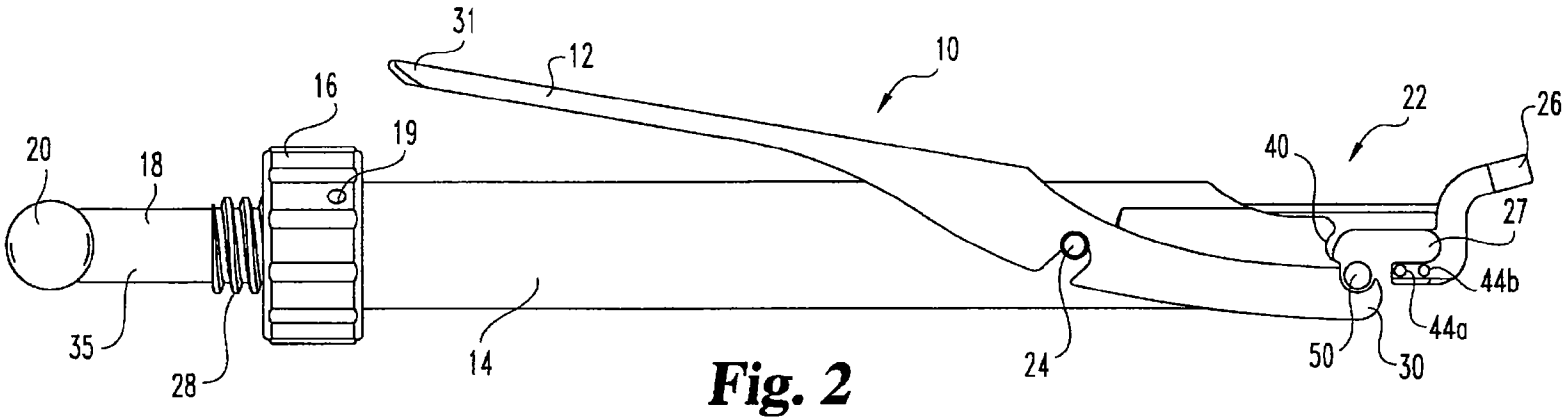
FIG. 2 is a side view of the rod introduction apparatus of FIG. 1.
Figure 3:
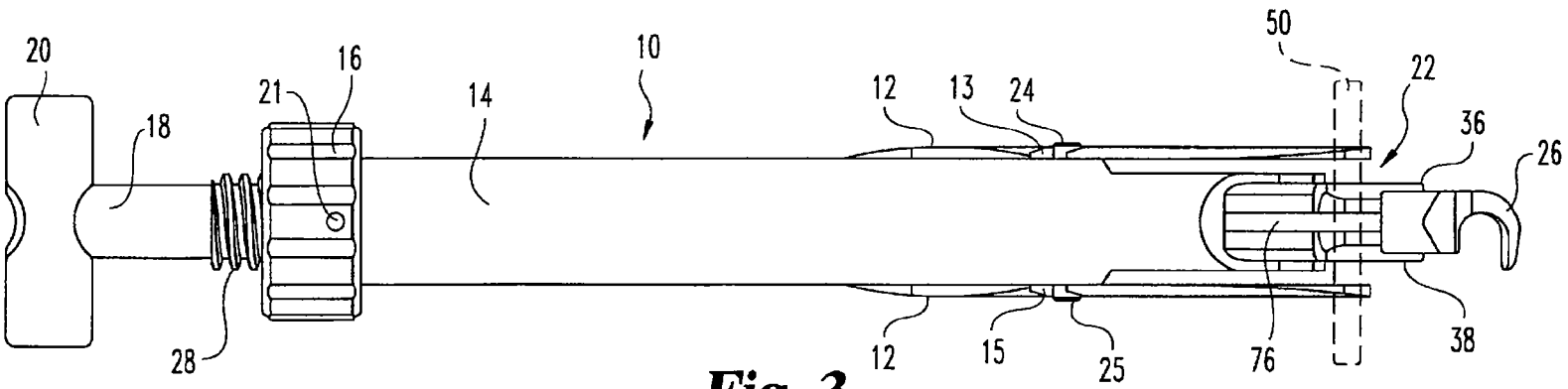
FIG. 3 is a bottom plan view of the rod introduction apparatus of FIG. 1.

Each clamping branch includes a series of projections 42a and 42b to engage corresponding recesses 44a and 44b on implant 26. While FIGS. 2 and 3 show implant 26 as a spinal hook, it is contemplated that the clamping branches may be adapted to engage a variety of implants, with or without the use of interengaging projections and recesses. In the preferred embodiment, each branch includes two projections 42a and 42b to engage a corresponding two recesses 44a and 44b on implant 26. However, it is contemplated that the number of projections on each clamping branch can vary, depending on the number of mating recesses disposed on implant 26. Moreover, it is contemplated that implant 26 may contain a series of projections while clamping branches may have corresponding recesses.

Disposed on the opposite end of clamp shaft 18 is T-handle 20. Adjacent T-handle 20 and spaced by a smooth cylindrical shank portion 35, are external threads 26 adapted to engage an internally threaded nut. Additionally, disposed between the treads 26 and the gripping nose 22 is a shoulder 86 where clamping shaft 18 transitions from a cylindrical cross section adjacent threads 26 to a substantially rectangular cross section extending to gripping nose 22.

Referring now to FIG. 10, clamp shaft 18 has a substantially uniform width when viewed from this side, with the exception of a reduced width portion disposed between shoulder 86 and gripping end 22. The reduced width area is defined by sidewalls 70 and 71 and continues at a reduced width until it begins to increase at ramped portions 72 and 73. Ramp portions terminate in sidewalls 74 and 75, having the same width as the remainder of the clamp shaft 18. In addition to the area of reduced outer width, in the area of reduced outer width, the walls also include reduced thickness sidewalls 80 and 82. This area of reduced thickness creates void 78. It will be understood that in use, as clamp shaft 18 is withdrawn into outer sleeve 14, outer sleeve side walls 60 and 61 will engage ramps 72 and 73, respectively, thereby urging clamping branches 36 and 38 toward one another and reducing the distance between the clamping branches. Moreover, it will be understood that a major portion of the deformation required to urge clamping branches 36, 38 toward one another will occur in the sidewalls defining cavity 78.

Figure 11A:
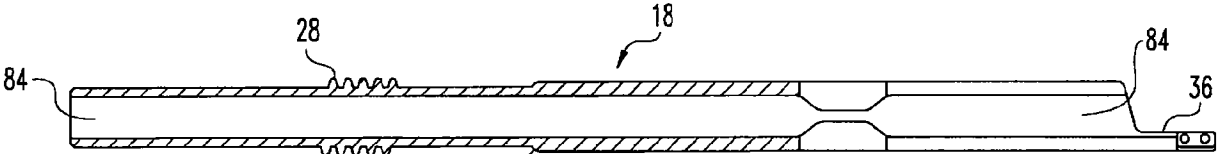
FIG. 11(a) is a cross-sectional view of the rod introduction clamp shaft taken along section lines 11—11.
Figure 11B:
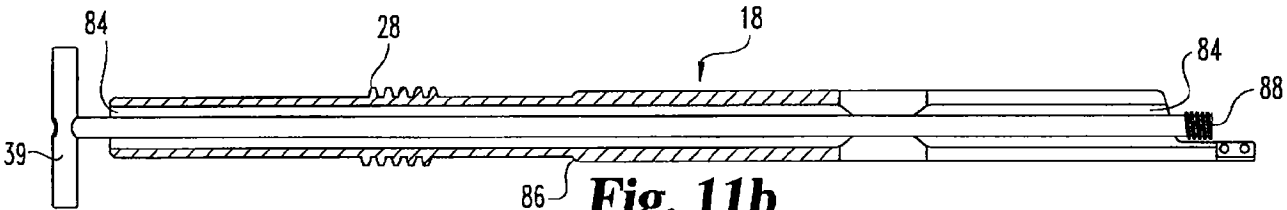
FIG. 11(b) is a cross-sectional view of the rod introduction clamp shaft showing a threaded plug and driving member extending through the cannula.

Referring now to FIG. 11(a), clamp shaft 18 has a central cannula 84 extending throughout the entire length of the shaft. Cannula 84 has a uniform diameter throughout and is adapted to receive a fastener for placement onto an implant. The internal passage for delivery of the fastening member to the implant provides an important advantage to the surgeon when the rod is being held in alignment with the implant because external passages to the implant may be obstructed or have limited clearance because of the presence of the rod reduction apparatus. In the preferred embodiment, an externally threaded plug 88 (FIG. 11(b)) may be placed into the cannula and urged into engagement with an internally threaded opening in hook 26. An elongated driving member 89 is then inserted through cannula 84 and engaged with threaded plug 88 to threadedly insert the plug into a corresponding threaded opening in the implant. Although an externally threaded plug is shown in this embodiment, it is contemplated that an internally threaded nut could be passed through cannula 84 to engage an externally threaded portion of a hook or a screw. The internally threaded nut could then be tightened by engagement of projections on a tightening tool with corresponding recesses in the nut.

Figure 12:
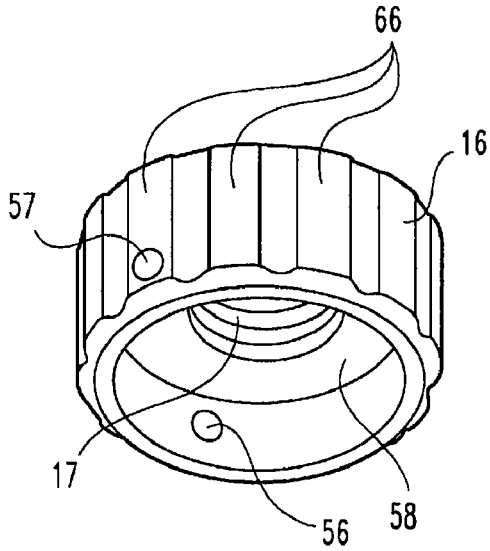
FIG. 12 is a perspective view of the rod introduction speed nut.
Figure 13:
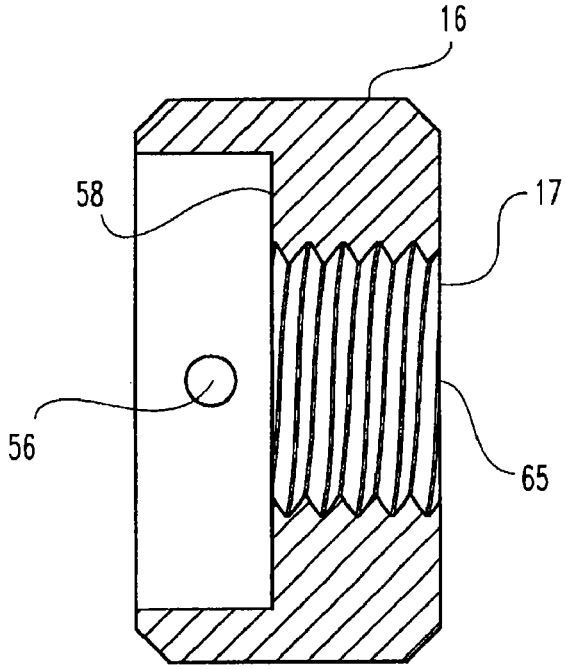
FIG. 13 is a cross-sectional view of the speed nut of FIG. 12.

Speed nut 16 of the present invention is of conventional design (FIGS. 12 and 13) and is rotatably mounted on outer sleeve 14. Speed nut 16 includes a central threaded opening 65 sized to freely slide over smooth shank portion 35 of clamping shaft 18. Threads 17 are adapted to engage cooperable threads 28 on clamping shaft 18. Bearing surface 58 surrounds threaded opening 65 and forms an internal bearing surface for bearing against outer sleeve 14. Extending through the sidewall of the nut 16 are a series of openings 56 and 57 (and a third opening not shown), each adapted to receive a retaining pin. In the preferred embodiment, speed nut 16 has a series of projections 66 on its outer surface for ease of gripping during the turning process.

Preferably, the rod insertion apparatus of the present invention includes a lateral approximator mechanism to bring an implant into alignment with a laterally offset longitudinal member. In the preferred embodiment, the lateral approximator mechanism is a lateral approximator lever 12 pivotally attached to outer sleeve 14 (FIG. 1). Lateral approximator lever 12 defines a pair of keyways 13 and 15 (FIG. 3) adapted to selectively engage a pair of pivot pins 24 and 24 on outer sleeve 14. The proximal end 31 of lever 12 is configured to be a handle for manually manipulating the lever to urge a laterally offset rod and implant into alignment.

The rod engaging end 30 of lever 12 is bifurcated into a first lever arm 29 and a second lever arm 33. Each arm freely passes over the outer surface of outer sleeve 14. First lever arm 29 has a rod engaging hook 32 disposed at its distal end. Likewise, second lever arm 33 has a corresponding rod engaging hook 34 disposed at its distal end and in alignment with engaging hook 32 permitting both hooks to contact a rod simultaneously. It is contemplated that the extent of lever arm extending distally beyond hooks 32 and 34 should be minimized in order to limit contact with surrounding anatomical structures during the lateral approximation procedure and the vertical reduction procedure if performed.

The above-described components of the rod introduction apparatus of the present invention are assembled as follows. Clamp shaft 18 as shown in FIGS. 9 through 11, is inserted into outer sleeve 14 with surfaces 70 and 72 aligned with surfaces 60 and 61 of the outer sleeve, respectively. Speed nut 16 is then passed over the proximal end 29 of clamp shaft 18 until bearing surface 58 abuts shoulder 46 on outer sleeve 14. A series of retaining pins 19, 21 and a third pin (not shown) are placed in the openings 56, 57 and a third opening in nut 16 (not shown). The retaining pins extend into the space between nut 16 and outer sleeve 14. Nut 16 is thereby retained on shoulder 46 by bearing surface 58 and a series of retaining pins.

In the preferred embodiment, T-handle 20 having a central opening aligned with cannula 84 is added for ease of manipulation of clamp shaft 18 within outer sleeve 14. In the preferred embodiment, T-handle 20 is welded onto clamp shaft 18, although it is contemplated that other means such as brazing or threading may be used to attach T-handle 20. It is contemplated that a separate handle is not required, instead, the surface of clamp shaft 18 may be roughened for easy gripping by the surgeon or the shaft may be machined to define an enlarged area for gripping. Finally, at the option of the user, lateral rod approximator lever slides about the outer surface of outer sleeve 14 to pass key way 13 and corresponding key way 15 on the opposite side of lever 12 over pivot pins 24 and 25, respectively. In the preferred embodiment, lateral approximator lever 12 can be selectively interconnected with the outer sleeve, thus permitting the lever to be added or removed at the user's discretion.

Figure 14:
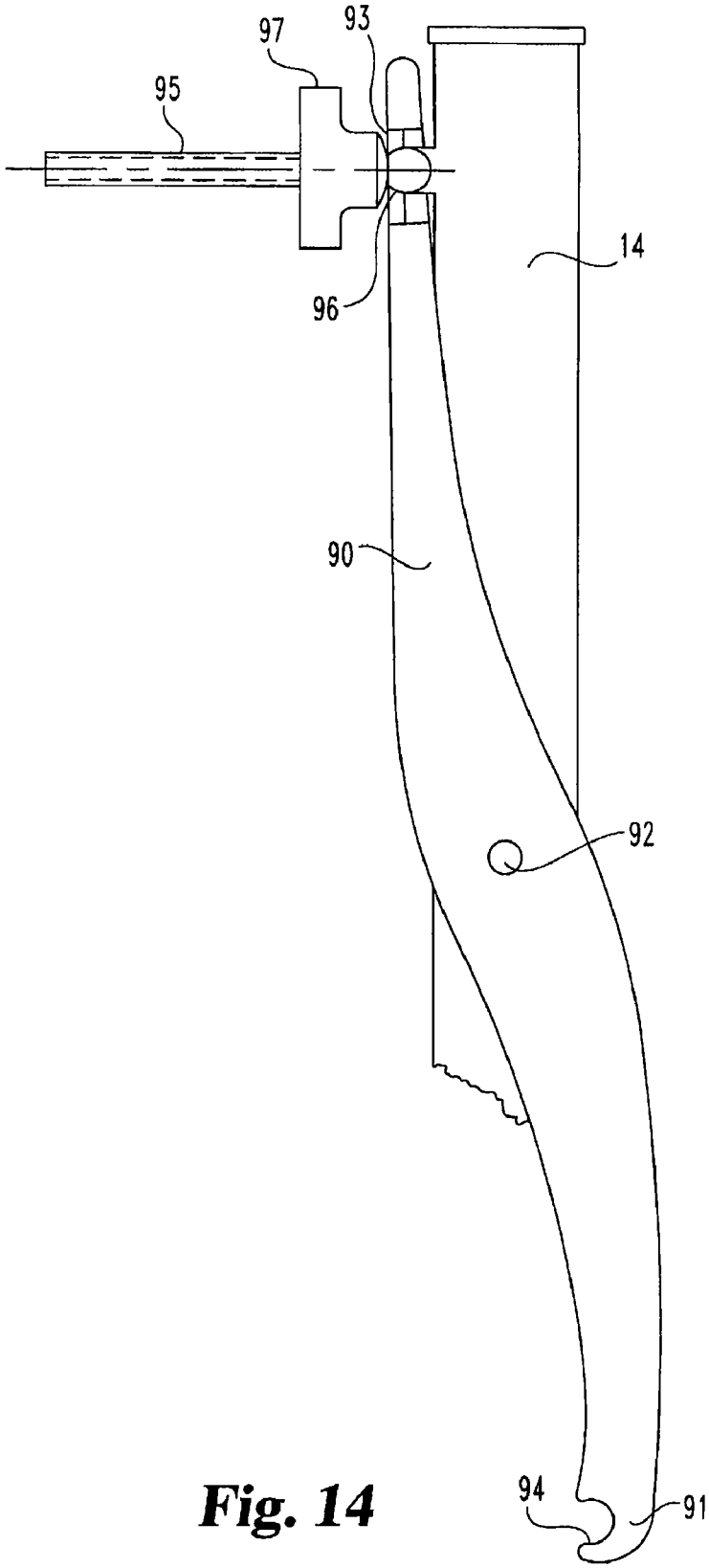
FIG. 14 is a partial side view of a lever mechanism according to another embodiment of the present invention.
Figure 15:
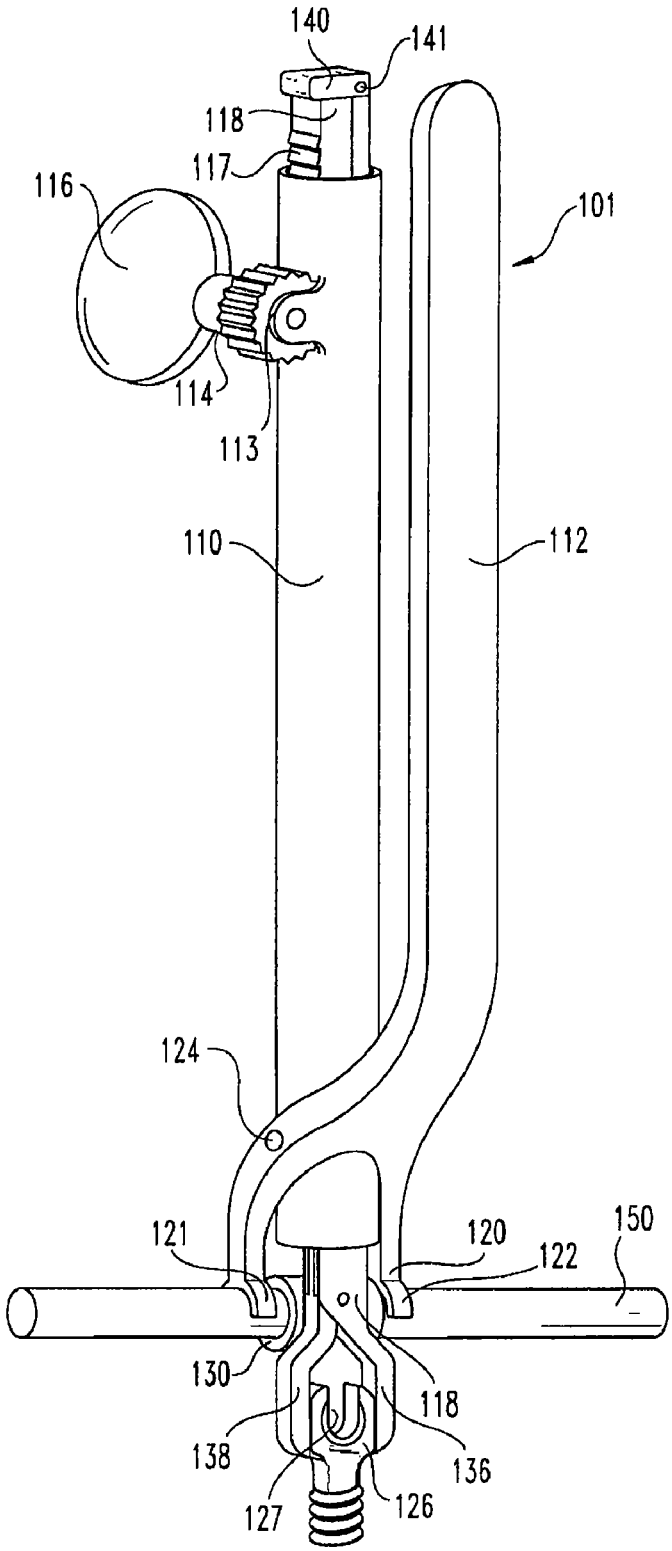
FIG. 15 is an alterative embodiment of a rod reduction apparatus according to the present invention.

As shown in FIG. 14, it is contemplated that a lateral approximator lever 90 having rod engaging end 91 with rod hook 94 could be pivotally attached to outer sleeve 14 in a non-removable fashion. In this embodiment, lever 90 is pivotally attached to outer sleeve 14 by a pivot pin 92 and a similar pivot pin (not shown) disposed on the opposite side of outer sleeve 14. Moreover, in this embodiment, lever 90 is provided with a mechanical means to urge the rod and implant into lateral alignment. The mechanical mechanism extends through oblong opening 93 in lever 90. A threaded shaft 95 is pivotally connected to outer sleeve 14 by a pin 96. An enlarged finger nut 97 is threaded onto threaded shaft 95 to urge lever 90 into the desired position.

Figure 4:
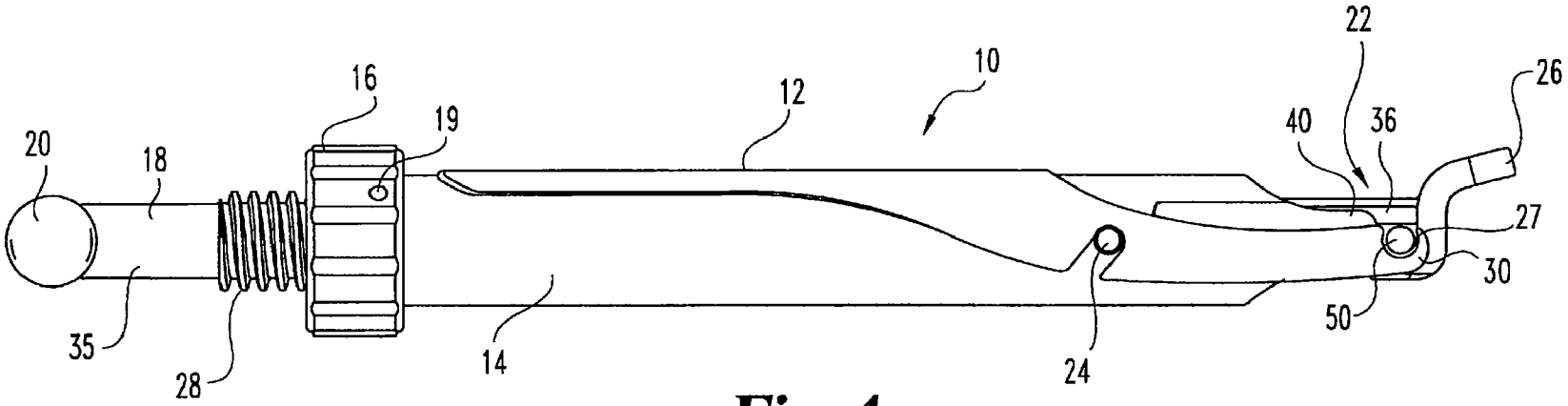
FIG. 4 is a side view of the rod introduction apparatus of FIG. 2 with the rod seated in the implant.
Figure 5:
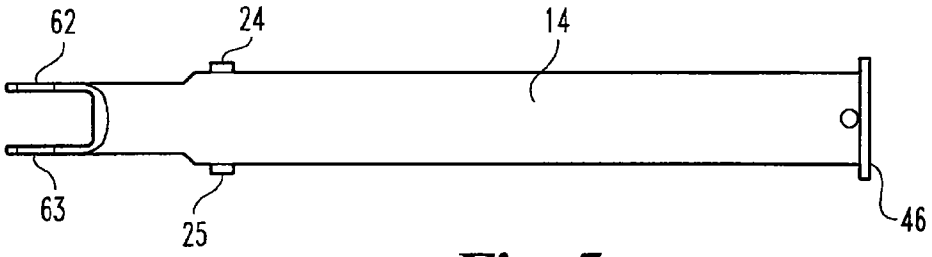
FIG. 5 is a top view of the rod introduction sleeve.

Referring now to FIGS. 2 through 4, in operation, the rod introduction apparatus of the present invention may be utilized to both laterally approximate a spinal rod to an implant having an opening for receiving a rod and to vertically reduce the rod into the opening of the implant. As will be appreciated by those skilled in the art, clamp shaft 18 is free to slide within outer sleeve 14 when threads 28 are not engaged with speed nut 16. In a first area of freedom of movement, clamp shaft 18 is free to move the length of smooth shank portion 35 disposed between threads 28 and T-handle 20. In this position, gripping nose 22 may be extended a substantial distance beyond the rod engagement end 40 of outer sleeve 14 into the insertion position in preparation for securely clamping an implant. It will be understood that with T-handle engaging speed nut 16, space 76 between clamping branches 36 and 38 will be at its maximum, thereby permitting the clamping branches to extend around an implant. As clamp shaft 18 is manually withdrawn into outer sleeve 14, ramp surfaces 72 and 73 of the clamp shaft bear against surfaces 60 and 61 of the outer sleeve, thereby urging clamping branches 36 and 38 toward one another and into the clamping position. It is contemplated that the action of drawing clamp shaft 18 within outer sleeve 14 is performed only after aligning projections 42 with the corresponding recesses 44 in the implant 26. In this manner, the implant may be securely gripped by the rod introduction apparatus of the present invention. At this point, speed nut 16 may be partially rotated to engage at least a portion of threads 28 in order to securely hold clamp shaft 18 in the clamping position.

Once the implant has been securely gripped, the spinal rod 50 may then be aligned with the opening in the implant, both laterally and vertically. For lateral approximation, lateral rod approximator lever 12 is positioned as previously described about the outer sleeve 14 and pivotally connected with pivot pins 24 and 25. As shown in FIG. 2, the upper end 31 of lever 12 is displaced from the body of outer sleeve 14, thereby pivoting about the pivot pins and extending the rod engaging portion 30 of the lever a sufficient distance laterally from the outer sleeve to securely engage spinal rod 50 within hooks 32 and 34. After hooks 32 and 34 are securely engaged with rod 50, the upper end 31 of lever 12 is urged back into alignment with outer sleeve 14, thereby urging spinal rod 50 into alignment with rod engagement end 40 of the outer sleeve. Once this position has been achieved, the vertical displacement between rod 50 and implant 26 may then be reduced. Speed nut 16 is rotated while engagement with threads 28 to urge gripping nose 22 of clamping shaft 18 to be drawn into outer sleeve 14. As the clamping shaft is drawn into the outer sleeve, rod engagement end 40 approaches gripping nose 22 and thereby forces rod 50 into implant opening 27. Once in the final position (FIG. 4), implant 26 may be secured to rod 50 by any number of means, which include a threaded plug or blocking sleeve. In the preferred embodiment, clamp shaft 18 includes a cannula 84 extending therethrough. Once the rod has been positioned within the opening 27 of implant 26, a threaded plug 88 is passed through cannula 84 until it seats into the correspondingly threaded opening in implant 26. A driving member extending through cannula 84 is used to tighten the plug in the implant. Threaded plug 88 securely holds the rod in the implant opening.

Once the rod has been secured to the implant, rod adjustability lever 12 is rotated away from engagement with outer sleeve 14, thereby releasing the rod 50. Further, speed nut 16 is rotated to urge gripping nose 22 out of outer sleeve 14 and thereby separate rod engagement end 40 from rod 50. Speed nut 16 is continued to be rotated until it no longer engages threads 28, which thereby allows clamp shaft 18 to slide within outer sleeve until handle 20 engages speed nut 16. This movement permits clamping branches 36 and 38 to assume the insertion position and thereby release the implant. Once released, the rod introduction apparatus of the present invention may then be withdrawn.

Referring now to FIGS. 15 through 19, an alternative embodiment of the rod introduction apparatus according to the present invention includes outer sleeve 110, clamping shaft 118, and lateral approximator lever 112. Similar to the first described embodiment, rod reduction apparatus 101 is capable of gripping an implant, engaging a laterally offset longitudinal member and aligning the implant and offset longitudinal member and reducing the vertical distance between the implant and longitudinal member.

Figure 16:
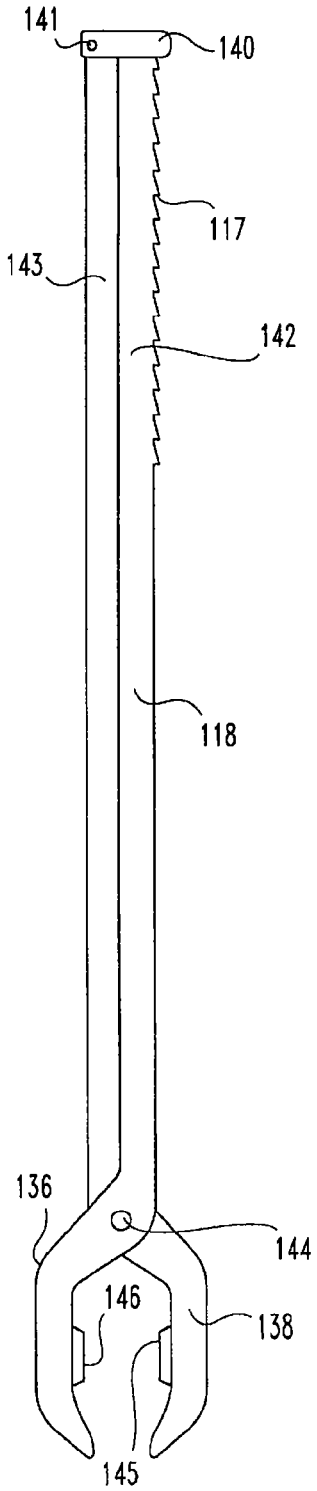
FIG. 16 is a front view of the clamp shaft of the embodiment of FIG. 15.
Figure 17:
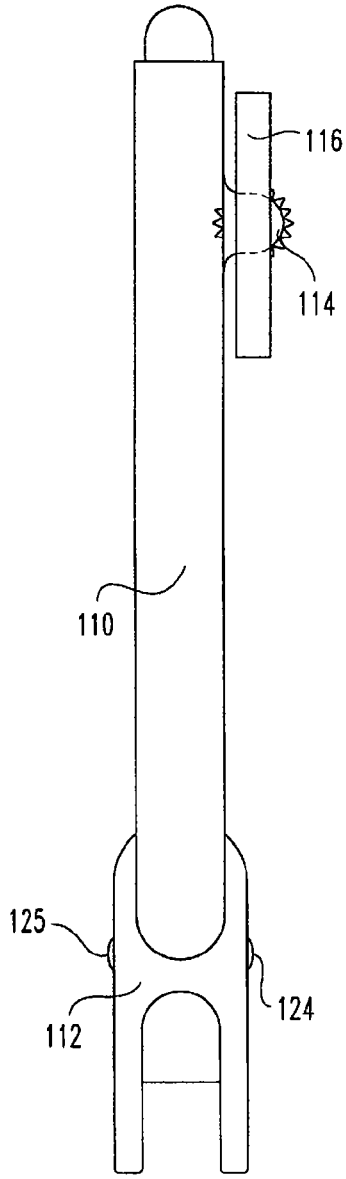
FIG. 17 is a front view of the outer sleeve of the embodiment of FIG. 16.

In this embodiment, clamping shaft 118 comprises two articulating branches 142 and 143 pivoting about a connecting pivot pin 144 (FIG. 16). While the branches illustrated do not define an internal cannula, it is contemplated that for certain applications it may be desirable that each branch form a portion of a cannula adapted for insertion of a fastener. Distally of pivot pin 144, articulating branches 142 and 143 define clamping branches 138 and 136, respectively. Clamping branches 136 and 138 have projections 146 and 145, respectively, adapted to engage corresponding recesses (not shown) in screw 126. Articulating movement of branches 142 and 143 moves clamping branches 136 and 138 between an insertion position with clamping branches spaced by a first larger distance and a clamping position with clamping branches spaced by a second smaller distance. The branches are held in the clamping position by retaining cap 140 pivotally connected to branch 143 and selectively engaging branch 142. Articulating branch 142 further includes a rack 117 disposed on its outer surface.

Outer sleeve 110 includes mounting brackets 113 and 144. An opening (not shown) is formed in the sidewall of outer sleeve 110 between mounting brackets 113 and 114. Pinion 116 is pivotally mounted to mounting brackets 113 and 144 with a portion of the pinion extending through the opening and into the interior channel of outer sleeve 110.

Figure 18:
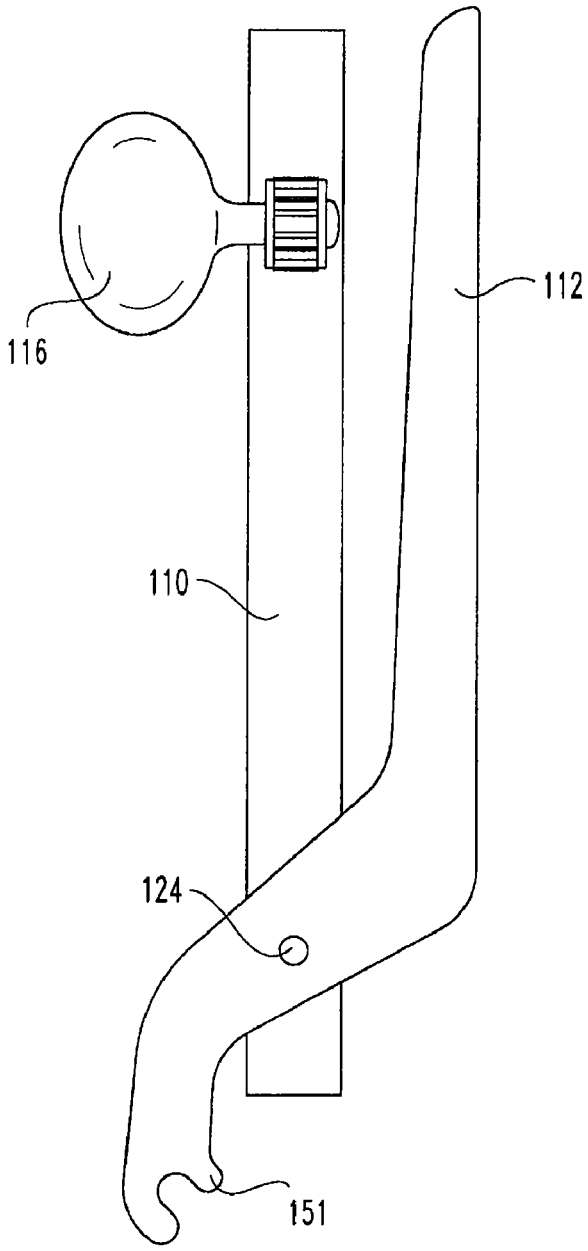
FIG. 18 is a side view of the outer sleeve of FIG. 17.
Figure 19:
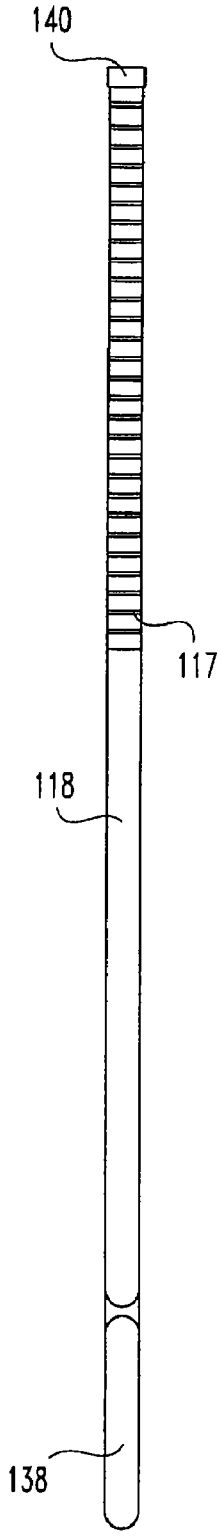
FIG. 19 is a side view of the clamp shaft of FIG. 16.

Lateral rod approximation lever 112 is pivotally mounted to outer sleeve 110 by pivot pins 124 and 125. The rod engaging end 120 of lever 112 includes a pair of hooks 121 and 122 for engaging a rod. As shown in FIG. 18, each hook includes an upper projection 151 for securely engaging the rod during vertical reduction.

In operation, articulating branches 142 and 143 are separated to position clamping branches 136 and 138 in the insertion position. The clamping branches are positioned adjacent screw 126 with projections 145 and 146 aligned with corresponding recesses (not shown) in screw 126. Articulating branches are then brought together, thereby urging projections into the screw recesses to securely hold the implant. Retaining cap 140 is then rotated about pin 141 until the cap securely engages articulating branch 142. In this manner, the branches remain in the clamping position.

After the implant has been securely clamped, outer sleeve 110 with interconnected lever 112 and pinion 116 is slid over clamping shaft 118 with pinion 116 aligned with rack 117 and is urged downwardly until pinion 116 engages rack 117. Lever 112 is then positioned to engage rod 150. Lever 112 is moved to bring rod 150 into lateral alignment with screw 126. Pinion 116 is then rotated to urge outer sleeve 110 towards screw 126 thereby urging engaged rod 150 into vertical alignment with screw 126. In the illustrated embodiment, screw 126 is a variable angle screw engagable by an eyebolt mechanism previously place on rod 150. Such an eyebolt attachment mechanism is offered by Sofamor Danek Group as the TSRH™ Variable Angle Eyebolt. Once in alignment, the eyebolt mechanism is utilized to securely interconnect the screw and rod.

Once screw and rod are interconnected, pinion 116 must be reversed to move outer sleeve 110 away from screw 126. Once pinion 116 is free of rack 117, outer sleeve 110 may be removed. Retaining cap 140 is then removed from articulating branch 142, thereby permitting the branches to disengage screw 126.

While the invention has been illustrated and described in detail in the drawings and foregoing description, the same is to be considered as illustrative and not restrictive in character, it being understood that only the preferred embodiments have been shown and described and that all changes and modifications that come within the spirit of the invention are desired to be protected.

What is claimed is:

[1. A multiple action insertion apparatus for engaging a longitudinal member and an implant, comprising:

an implant holder including a first clamping branch and a second clamping branch cooperable with said first clamping branch to hold to an implant;

a reduction mechanism interconnected with said implant holder, said reduction mechanism having a distal end for engaging the longitudinal member, wherein said reduction mechanism urges the longitudinal member into vertical alignment with the implant; and a lateral approximator mechanism interconnected with said implant holder, said lateral approximator mechanism having a distal end disposed adjacent said first and second clamping branches, said distal end adapted to engage the longitudinal member, wherein said lateral approximator mechanism urges the longitudinal member into lateral alignment with the implant.]

[2. The insertion apparatus of claim 1, wherein said lateral approximator mechanism is a lever arm pivotally connected to said implant holder.]

3. [The insertion apparatus of claim 1,] *A multiple action insertion apparatus for engaging a longitudinal member and an implant, comprising:*

*an implant holder including a first clamping branch and a second clamping branch cooperable with, and movable relative to, said first clamping branch to hold to an implant;*

*a reduction mechanism interconnected with said implant holder, said reduction mechanism having a distal end for engaging the longitudinal member, wherein said reduction mechanism urges the longitudinal member into vertical alignment with the implant; and*

*a lateral approximator mechanism interconnected with said implant holder, said lateral approximator mechanism having a distal end disposed adjacent said first and second clamping branches, said distal end adapted to engage the longitudinal member, wherein said lateral approximator mechanism urges the longitudinal member into lateral alignment with the implant,* wherein said implant holder comprises a shaft having a gripping end with a portion, said gripping end defining a first clamping branch and a cooperable second clamping branch, said first and second clamping branches tending to assume an insertion position defining a first distance between said first and second clamping branches, and said first and second clamping branches compressible into a clamping position defining a second distance between said first and second clamping branches, said first distance greater than said second distance; and a sleeve defining an interior channel, said shaft slidably received within said interior channel, said shaft moveable between a first position with said portion extending from said sleeve and a second position with said portion drawn into said sleeve;

wherein movement of said shaft within said tubular sleeve from said first position to said second position controls said first and second clamping branches from said insertion position to said clamping position.

4. The introduction apparatus of claim 3, wherein said reduction apparatus comprises a series of external threads disposed on said shaft and an internally threaded nut rotatably mounted on said sleeve, said internally threaded nut cooperable with said external threads, said sleeve further defining a bearing surface adjacent said gripping end for engaging the longitudinal member, wherein rotation of said nut moves said shaft with respect to said sleeve and urges said bearing surface against the longitudinal member thereby reducing the distance between the longitudinal member and the implant.

5. The introduction apparatus of claim 4, wherein the longitudinal member is a rod and said bearing surface is a recessed area on said sleeve.

[6. A multiple action insertion apparatus for engaging a longitudinal member and an implant, comprising:

means for attaching to an implant;

means for lateral approximation of a longitudinal member laterally offset from the implant, said means for lateral approximation interconnected with said means for attaching; and means for vertical reduction of the longitudinal member vertically offset from the implant, said means for vertical reduction interconnected with said means for attaching, wherein said means for lateral approximation laterally aligns the longitudinal member over the implant and said means for vertical reduction vertically aligns the longitudinal member with the implant.]

[7. An implant holder for holding an implant adapted to receive a fastener, comprising:

means for gripping the implant said means for gripping including a gripping end and a handle defining a longitudinal cannula having a distal end adjacent said gripping end, said cannula adapted to receive a fastener cooperable with said implant;

wherein said means for gripping includes a first clamping branch and a second clamping branch defining said gripping end, said first and second clamping branches aligned in a spaced relationship and cooperable to engage the implant, and wherein said handle defines a series of threads opposite said gripping end, and further including a sleeve defining an internal channel adapted to receive at least a portion of said gripping end and said handle, and a nut rotatably mounted on said sleeve, said nut cooperable with said threads on said handle.]

[8. The implant holder of claim 7, wherein said sleeve has a distal end adjacent said gripping end and said sleeve defines a bearing surface adapted to bear against a longitudinal member, wherein rotation of said nut draws said handle into said sleeve and thereby reduces the distance between the implant engaged by said first and second clamping branches and the longitudinal member bearing against said bearing surface of said sleeve.]

[9. The implant holder of claim 8, further including a lateral approximating lever pivotally attached to said sleeve.]

10. An implant holder for gripping an implant, comprising:

a shaft having a gripping end with a portion, said gripping end defining a first clamping branch and a cooperable second clamping branch, said first and second clamping branches tending to assume an insertion position defining a first distance between said first and second clamping branches, and said first and second clamping branches compressible into a clamping position defining a second distance between said first and second clamping branches, said first distance greater than said second distance; [and]

a sleeve defining an interior channel, said shaft slidably received within said interior channel, said shaft moveable between a first position with said portion extending from said sleeve and a second position with said portion drawn into said sleeve; *and*

*an actuating mechanism for moving said shaft within said tubular sleeve, said actuating mechanism provided about said tubular sleeve and an actuating force for operating said actuating mechanism applied about the tubular sleeve,* wherein movement of said shaft within said tubular sleeve from said first position to said second position controls said first and second clamping branches from said insertion position to said clamping position.

11. The implant holder of claim 10, wherein said sleeve defines an engagement surface for engaging a longitudinal member to be interconnected with said implant, whereby positioning said shaft in said second position clamps the implant and further movement of said inner shaft into said sleeve urges the implant into alignment with the longitudinal member.

12. The implant holder of claim 11, [further including means for controlling the position of said shaft within said sleeve] *wherein said actuator mechanism comprises threads provided about the central opening of said tubular sleeve*.

13. The implant holder of claim 12, wherein said [means for controlling] *actuator mechanism* includes an external thread disposed on said inner shaft and a nut rotatably mounted on said tubular sleeve, said nut having an internal thread corresponding to said external thread, whereby said inner shaft may be drawn into said outer sleeve by rotation of said nut.

14. The implant holder of claim 11, wherein said *threads on said* shaft [includes] *are formed as* a series of external threads and *said shaft* further [including] *includes* an internally threaded nut rotatably mounted on said sleeve, said internally threaded nut cooperable with said external threads, wherein rotation of said nut moves said shaft with respect to said sleeve.

15. The implant holder of claim 14, further including a lateral approximator lever pivotally engaging said sleeve, said lateral approximator lever having a rod engaging end adapted to engage a laterally offset rod, wherein upon engaging a laterally offset rod, said lateral approximator lever may be pivoted toward said sleeve, thereby positioning the rod adjacent the implant.

16. The implant holder of claim 15, wherein said first and second clamping branches each have a distal end and include at least one projection defined on each of said distal ends.

17. The implant holder of claim 10, wherein said shaft includes a handle disposed opposite said gripping, said handle utilized to position said shaft within said sleeve.

18. The implant holder of claim 10, wherein said shaft is cannulated to slidingly receive a fastening member adapted to be engaged with the implant.

19. The implant holder of claim 10, wherein said attachment to said implant is a non-pivotal attachment.

20. The implant holder of claim 10, further including a lateral approximator lever pivotally engaging said sleeve, said lateral approximator lever having a rod engaging end adapted to engage a laterally offset rod, wherein upon engaging a laterally offset rod, said lateral approximator lever may be pivoted toward said sleeve, the rod is positioned adjacent the implant.

21. The implant holder of claim 20, wherein said lateral approximator lever removably engages said sleeve, whereby said lever may be selectively removed.

22. The implant holder of claim 10, wherein said first and second clamping branches each have a distal end and include at least one projection defined on said distal end.

23. The implant holder of claim 10, wherein said shaft defines a cannula having a distal end adjacent said first and second clamping branches, said cannula adapted to slidingly receive a fastener, whereby said fastener is delivered through said cannula to said distal end for interengagement with the implant.

24. An implant holder having a rod reduction mechanism for vertically aligning a longitudinal member and an implant, comprising:

means for gripping the implant;

a sleeve having an axis and a distal end adapted to engage the longitudinal member, said sleeve having an axial bore sized to receive said means for gripping, said means for gripping slidably received within said axial bore; and

*threaded* means for axially displacing said sleeve with respect to said means for gripping, whereby a [vertical] *vertically* offset longitudinal member is urged into alignment with the implant.

25. The implant holder of claim 24, wherein said means for gripping are articulating forceps.

26. The implant holder of claim 24, wherein said means for axial displacement includes a series of threads disposed on said means for gripping and a nut rotatably mounted on said sleeve and threadedly engagable with said threads.

27. The implant holder of claim 24, wherein said means for axial displacement includes a rack disposed on said means for gripping and a pinion pivotally mounted on said sleeve and interengagable with said rack.

28. A method for interconnecting a longitudinal member and an implant adapted to engage the longitudinal member, comprising the steps of:

providing an introduction apparatus having an attachment mechanism with a cannula and a vertical reduction mechanism;

attaching the introduction apparatus to the implant;

operating the vertical reduction mechanism, *by actuating a threaded engagement mechanism of the vertical reduction mechanism,* to force the longitudinal member into alignment with the implant;

inserting a fastener through the cannula;

interconnecting the fastener and the implant, wherein the longitudinal member is securely attached to the implant; and removing the introduction apparatus.

[29. A method for interconnecting a longitudinal member and an implant adapted to engage the longitudinal member, comprising the steps of:

providing an introduction apparatus having an attachment mechanism, a lateral approximation lever, and a vertical reduction mechanism;

attaching the introduction apparatus to the implant;

engaging a laterally offset longitudinal member with one end of the lateral approximator lever;

rotating the lever to urge the longitudinal member into lateral alignment with the implant;

operating the vertical reduction mechanism to force the longitudinal member into vertical alignment with the implant; and interconnecting the longitudinal member and the implant.]

30. [The method of claim 29.] *A method for interconnecting a longitudinal member and an implant adapted to engage the longitudinal member, comprising the steps of:*

*providing an introduction apparatus having an attachment mechanism, a lateral approximation lever, and a vertical reduction mechanism;*

*attaching the introduction apparatus to the implant;*

*engaging a laterally offset longitudinal member with one end of the lateral approximator lever;*

*rotating the lever to urge the longitudinal member into lateral alignment with the implant;*

*operating the vertical reduction mechanism to force the longitudinal member into vertical alignment with the implant; and*

*interconnecting the longitudinal member and the implant,* wherein the providing step includes providing attachment mechanism having a cannula and further including the step of delivering a fastener through the cannula and to the implant prior to interconnecting the longitudinal member and the implant.

*31. A method for interconnecting a longitudinal member and an implant adapted to engage the longitudinal member, comprising the steps of:*

*providing an introduction apparatus having an attachment mechanism with attachment prongs for attaching to the implant, a cannula and a vertical reduction mechanism;*

*attaching the introduction apparatus to the implant;*

*operating the vertical reduction mechanism to force the longitudinal member into alignment with the implant;*

*inserting a threaded fastener through the cannula;*

*interconnecting the fastener and the implant, wherein the longitudinal member is securely attached to the implant; and*

*removing the introduction apparatus,*

*wherein the introduction apparatus further comprises an elongated member that extends through the cannula, the elongated member engaging the fastener in said interconnecting step to cause the fastener to interconnect with the implant.*

*32. The method of claim 31, wherein the attachment prongs are formed on the proximal end of the cannula.*

*33. The method of claim 32, wherein the implant is a bone screw.*

*34. The method of claim 33, wherein the longitudinal member is an implantable rod.*

*35. The method of claim 32, wherein the elongated member is separate from the vertical reduction mechanism.*

*36. The method of claim 32, wherein the introduction apparatus further comprises an actuator for operating the vertical reduction mechanism in said operating step, and the actuator connects to the distal end of the cannula about a circumference of the distal end.*

*37. The method of claim 36, wherein the implant contains a threaded opening that receives the threaded fastener in said interconnecting step.*

*38. The method of claim 31, wherein the operating and inserting steps take place separately.*

*39. An implant holder for gripping an implant, comprising:*

*a shaft having a gripping end with a portion, said gripping end defining a first clamping branch and a cooperable second clamping branch, said first and second clamping branches tending to assume an insertion position defining a first distance between said first and second clamping branches, and said first and second clamping branches compressible into a clamping position defining a second distance between said first and second clamping branches, said first distance greater than said second distance; and*

*a sleeve defining an interior channel, said shaft slidably received within said interior channel, said shaft moveable between a first position with said portion extending from said sleeve and a second position with said portion drawn into said sleeve;*

*wherein movement of said shaft within said tubular sleeve from said first position to said second position controls said first and second clamping branches from said insertion position to said clamping position, and*

*wherein said implant holder further comprises an actuator for moving said shaft relative to said tubular sleeve, said actuator comprising a first portion engaging a first side of said sleeve and a second portion engaging a second*

*side of said sleeve opposite said first side, said first and second portions moving relative to said shaft to actuate movement of said sleeve.*

*40. A system for spinal, surgery comprising:*

*said implant holder of claim 39;*

*a series of implants; and*

*a longitudinal member,*

*wherein said implant holder grips each of said series of implants, and*

*wherein the relative movement of said shaft and said tubular sleeve of said implant holder operate to reduce said longitudinal member to connect to an implant of said series of implants.*

*41. The system of claim 40, wherein said series of bone implants are bone screws and said longitudinal member is a rod.*

*42. The system of claim 41, wherein said shaft defines a passage through which a fastener for fastening said rod to a bone screw is insertable, while said first and second clamping branches grip said bone screw in the clamping position.*

*43. The system of claim 42, wherein a distal opening of said sleeve has an arcuate engaging edge for engaging said rod when said shaft and said sleeve are actuated relative to each other, said engaging edge operating to reduce said rod.*

*44. The system of claim 43, wherein said actuator is symmetrical with respect to opposing sides of said shaft.*

*45. A system for spinal surgery comprising:*

*the insertion apparatus of claim 40;*

*a series of implants; and*

*a longitudinal member,*

*wherein said implant holder grips each of said series of implants, and*

*wherein the relative movement of said shaft and said tubular sleeve of said implant holder operate to reduce said longitudinal member to connect to an implant of said series of implants.*

*46. A system for spinal surgery comprising:*

*said implant holder of claim 10;*

*a series of implants; and*

*a longitudinal member,*

*wherein said implant holder grips each of said series of implants, and*

*wherein the relative movement of said shaft and said tubular sleeve of said implant holder operate to reduce said longitudinal member to connect to an implant of said series of implants.*

* * * * *